United States Patent [19]

Thompson

[11] Patent Number: 4,500,722
[45] Date of Patent: Feb. 19, 1985

[54] VOLATILE METAL COMPLEXES

[75] Inventor: David A. Thompson, Horseheads, N.Y.

[73] Assignee: Corning Glass Works, Corning, N.Y.

[21] Appl. No.: 418,061

[22] Filed: Sep. 15, 1982

[51] Int. Cl.$^3$ .............................................. C07D 307/04
[52] U.S. Cl. ..................................... 549/429; 549/206
[58] Field of Search ................................ 549/206, 429

[56] References Cited

U.S. PATENT DOCUMENTS 4,243,597  1/1981  Hall et al. ............................ 549/206

OTHER PUBLICATIONS

Robert E. Sievers et al., Science, vol. 201, No. 4352, Jul. 21, 1978, pp. 217–223.
S. C. Chattoraj et al., J. Inorg. Nucl. Chem., (1966), vol. 28, pp. 1937–1943.

*Primary Examiner*—Norma S. Milestone
*Attorney, Agent, or Firm*—K. van der Sterre

[57] ABSTRACT

Novel β-diketonate complexes incorporating a tetrahydrofuran adduct, having the formula $M(hfa)_2 \cdot nTHF$ wherein M is Mg or Zn and n is in the range of about 1–4 and, which offer high volatility and good chemical stability at vaporization temperatures, are described.

1 Claim, 5 Drawing Figures

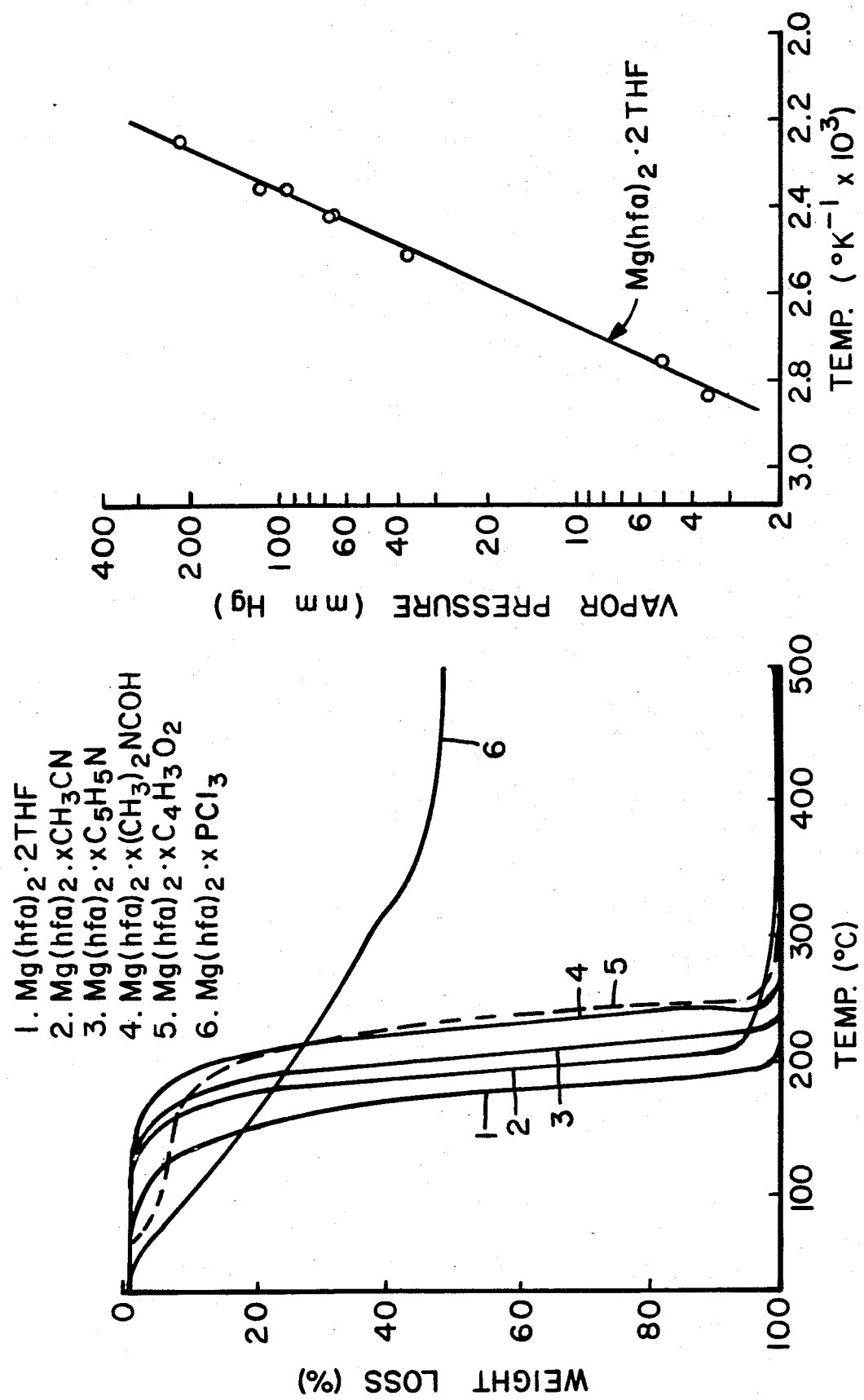

VOLATILE METAL COMPLEXES

BACKGROUND OF THE INVENTION

The present invention relates to organometallic compounds, and particularly relates to β-diketonate complexes of magnesium and zinc which exhibit unusually high volatility.

Volatile metal complexes are of interest for a variety of applications including fuel additives, metal vapor sources, and gas transport reagents. A useful discussion of β-diketonate complexes and their uses is provided by R. E. Sievers et al. in *Science* 201 [4352], pages 217–223 (July 1978), wherein numerous references to these complexes and methods for their preparation are cited.

The metal complexes or chelates of the anion of hexafluoroacetylacetone 1,1,1,5,5,5,-hexafluoro-2,4-pentanedione), having the formula $[CF_3-CO-CH-CO-CF_3]^-$ and hereinafter abbreviated (hfa)$^-$ have been the specific objects of study. For example, the complexes $Cd(hfa)_2$, $Mg(hfa)_2$ and $Zn(hfa)_2$ are known, although these complexes are most frequently isolated as adducts with the solvents used in their preparation, such as $H_2O$ and $NH_3$. The adducted complexes $Cd(hfa)_2.NH_3.H_2O$, $Cd(hfa)_2.2H_2O$ and $Zn(hfa)_2.2H_2O$, the latter being referred to as hydrates, have been prepared and reported by S. C. Chattoraj et al. in *J. Inorg. Nucl. Chem.* 28 (1966) pages 1937–1943.

SUMMARY OF THE INVENTION

The present invention provides novel adducted complexes of both magnesium and zinc which exhibit unusual stability and volatility. The complexes of the invention are tetrahydrofuran (THF) adducts of magnesium and zinc hexafluoroacetylacetonates, i.e., complexes of these metals with 1,1,1,5,5,5,-hexafluoro-2,4-pentanedione which are isolated as adducts with THF.

Complexes provided in accordance with the invention have the molecular structure; $M(hfa)_2.nTHF$ wherein M is Zn or Mg and n is in the range of about 1–4. The proportions of THF adduct present in the isolated complexes depend upon the metal selected and upon the process used to prepare the complex. For the adducted Mg complexes, n is typically 2–4, while for the Zn complexes n is in the range of 1–2.

BRIEF DESCRIPTION OF THE DRAWINGS

The invention may be further understood by reference to the drawings, wherein:

FIG. 1 contains thermogravimetric curves for selected adducted $Mg(hfa)_2$ complexes;

FIG. 2 contains a vapor pressure plot for a selected adducted $Mg(hfa)_2$ complex of the invention;

DETAILED DESCRIPTION

Figure 3:
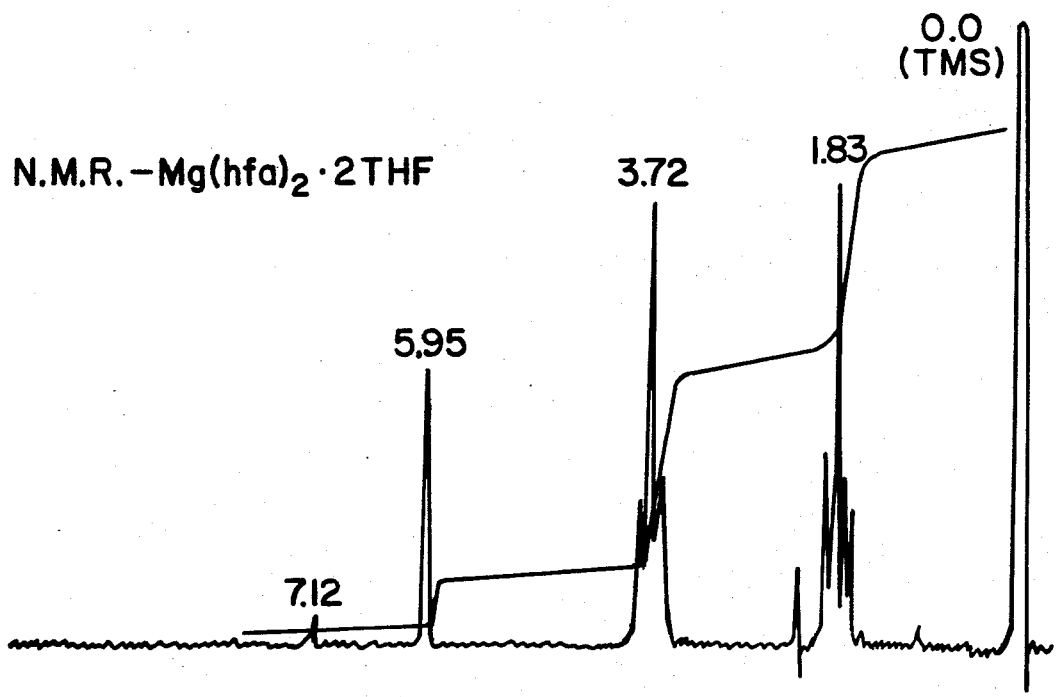
FIGS. 3–4 are proton nuclear magnetic resonance spectra for selected $Mg(hfa)_2.nTHF$ complexes provided in accordance with the invention.

The volatility of metal β-diketonate complexes depends not only upon the selection of the diketone used to form the complex but also, for each possible diketone, upon the presence or absence and nature of any adduct present within the molecule. β-diketonate complexes are known to form adducts with solvents used in their preparation, particularly when the complex is not coordinatively saturated and the solvent is a good Lewis base. The resulting adducted β-diketonate complexes can be quite stable relative, for example, to the hydrates of the complexes, and can themselves exhibit sufficient stability and volatility to constitute useful metal vapor sources. Examples of compounds which form adducts with β-diketonates are ammonia, water, ether, pyridine, bipyridyl, phenanthroline, tetrahydrofuran and dimethylformamide. These molecules attach to the complex as additional ligands to achieve six-fold or higher coordination with the metal nucleus.

The present invention is founded on the discovery that certain tetrahydrofuran adducts of $Mg(hfa)_2$ and $Zn(hfa)_2$ exhibit better stability, lower melting temperatures, and somewhat higher volatility than other adducts of these complexes. Thus these THF adducts can be maintained as liquids at lower temperatures and can be volatilized more rapidly and completely than the non-adducted complexes or other adducts thereof, rendering them particularly useful, for example, as sources of metal vapors for vapor phase reactions. The THF adduct of $Mg(hfa)_2$ can be prepared via the reaction of the diketone with basic magnesium carbonate in ether to produce the ether-water adduct, as illustrated by the following example.

EXAMPLE 1

A 2.5 g sample of basic magnesium carbonate, $4MgCO_3.Mg(OH)_2.nH_2O$ (n≈6) is suspended in 100 ml of diethyl ether with stirring under nitrogen. A 10.41 g sample of the pure β-diketone (Hhfa) is added to the suspension and the mixture is refluxed for two hours. The ether is then separated from a solid residual phase by filtration and evaporated to dryness. Evaporation of the ether phase leaves a residual white powder product identified as the ether-water adduct of magnesium hexafluoroacetylacetonate, $Mg(hfa)_2.1.5Et_2O.H_2O$.

THF adducts of $Mg(hfa)_2$ can be prepared from the water adduct by adding 20 ml of THF to the residue, which consists of about 1–2 g of material. This mixture is refluxed for 1 hour.

The resulting THF solution is dried by rotary evaporation to leave a white powder residue which is identified by proton nuclear magnetic resonance as $Mg(hfa)_2.4THF$.

The $Mg(hfa)_2.2THF$ adduct can be prepared from $Mg(hfa)_2.4THF$ by sublimation of the latter into a dry ice-cooled cold trap. The sublimed product, also a white powder, has a melting point of approximately 130° C., and the liquid can readily be vaporized at 160° C. to generate Mg-containing vapors without significant decomposition.

COMPARATIVE EXAMPLES

A comparison of the properties of the stable adduct $Mg(hfa)_2.2THF$ with other adducts of this hfa complex can be made by thermogravimetric analysis. Other adducts can be prepared by reacting the ether-water adduct of $Mg(hfa)_2$ produced in accordance with Example 1 above with selected ligands L to form adducted complexes of the formula: $Mg(hfa)_2.xL$, wherein L is the selected ligand and x is the number of ligand molecules present in the product.

Each adduct may be prepared in accordance with a procedure wherein 80 ml of diethyl ether is placed in a magnetically stirred flask and 2 ml of the appropriate ligand is added to the ether with stirring. A 2 g sample of $Mg(hfa)_2.1.5Et_2O.H_2O$ is then added with stirring and stirring is continued overnight. After stirring, each solution is evaporated to dryness to give a white powder or oil.

Examples of adducted complexes which can be produced as described above are reported in Table I below. All are produced as powder products except the dimethylformamide (DMF) adduct, which is isolated as an oil but dries to a powder in air. All products may be sublimed in vacuum at the temperatures reported in the Table. The proportions of adduct ligands present in each complex (the value of x above) have not been determined; however infrared spectra recorded between 4000–400 cm$^{-1}$ of samples mixed in KBr discs confirm the presence of ligand in the sublimed sample.

TABLE I

| Ligand | Adducted Complex | Sublimation Temp. (Vacuum) |
| --- | --- | --- |
| pyridine | Mg(hfa)$_2$.C$_5$H$_5$N | 80°–120° C. (residue left) |
| acetonitrile | Mg(hfa)$_2$.CH$_3$CN | 135°–155° C. (residue left) |
| PCl$_3$ | Mg(hfa)$_2$.PCl$_3$ | no sublimation below 190° C. |
| dioxane | Mg(hfa)$_2$.C$_4$H$_8$O$_2$ | 130°–160° C. (residue left) |
| dimethyl formamide | Mg(hfa)$_2$.(CH$_3$)$_2$NCOH | 100°–130° C. (no residue) |

FIG. 1 of the drawing sets forth thermogravimetric analysis curves useful for comparing the volatility and stability of Mg(hfa)$_2$.2THF with other adducts such as shown in Table I. All data for these curves is generated using sublimed samples of the adducts, except for the PCl$_3$ adduct which does not readily sublime.

Referring to FIG. 1, good stability in a complex is evidenced by rapid weight loss in the sample over a narrow temperature range to approximately 100% weight loss, with no weight loss occurring thereafter even at very high temperatures. The temperature at which one-half of the sample has been evaporated (T$_{\frac{1}{2}}$) is a good indicator of the volatility of the adducted complex.

The excellent stability and superior volatility of Mg(hfa)$_2$.2THF when compared with other adducts of Mg(hfa)$_2$ are evident from a study of FIG. 1. No evidence of thermal decomposition of the THF adduct is seen, and the sample exhibits about 99.5% evaporation at 200° C. The 50% volatilization temperatures (T$_{\frac{1}{2}}$) for the various adducts are reported in Table II below, opposite the formula for the Lewis base which reacts with the diketonate (Lewis acid) to form the adduct or complex.

TABLE II

| Lewis Base | Adduct Volatility T$_{\frac{1}{2}}$(°C.) |
| --- | --- |
| THF(C$_4$H$_8$O) | 180 |
| CH$_3$CN | 200 |
| C$_5$H$_5$N | 212 |
| C$_4$H$_8$O$_2$ | 235 |
| (CH$_3$)$_2$NCOH | 235 |
| PCl$_3$ | Decomposed |

The stable THF adduct of Mg(hfa)$_2$ also exhibits unexpectedly high vapor pressure when compared with many other adducted β-diketonates. FIG. 2 of the drawing plots the vapor pressure of this complex as a function of temperature over the temperature range of about 80°–175° C. Vapor pressures for this complex fall within the range of about 4–200 mm Hg over this temperature range.

Figure 4:
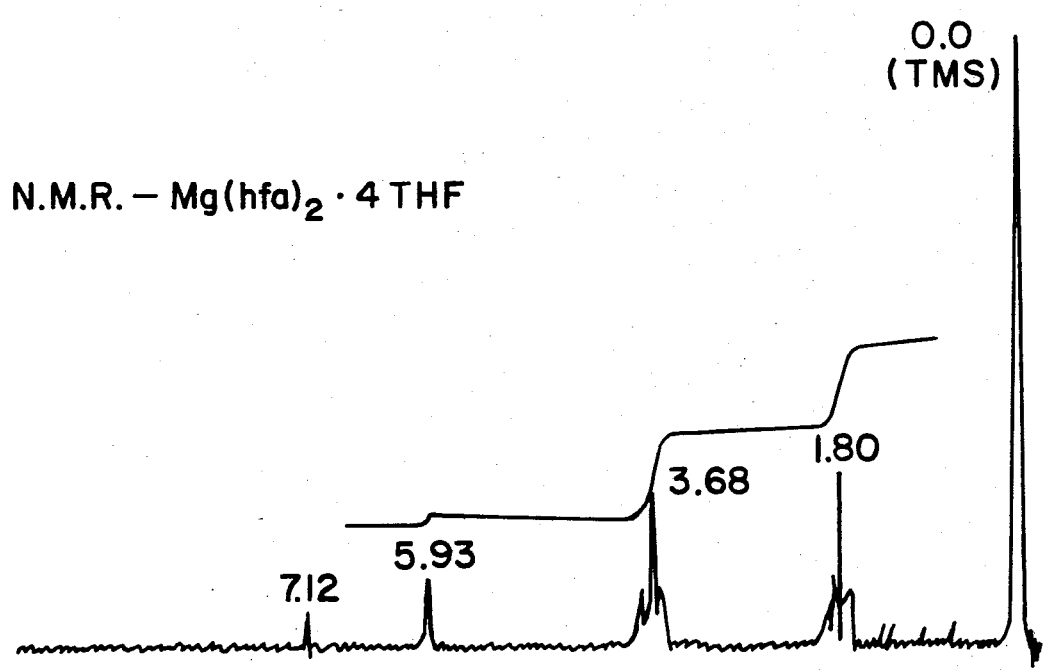

FIGS. 3 and 4 of the drawing are proton nuclear magnetic resonance spectra for the compounds Mg(hfa)$_2$.2THF and Mg(hfa)$_2$.4THF, both in a CDCl$_3$ solvent against a tetramethyl silane (TMS) standard. FIG. 3 is for the 2 THF adduct after sublimation in vacuum, whereas FIG. 4 is for the 4THF adduct as prepared in accordance with Example 1 prior to sublimation. The proton nmr data and elemental chemical analysis establish with good certainty the proportions of THF adduct present in each of the complex compounds.

The preparation of the water adduct of Zn(hfa)$_2$ has been described by Chattoraj et al. in *J. Inorg. Nucl. Chem.*, supra. A suitable procedure comprises reacting zinc oxide with Hhfa in the presence of water. Ten grams of ZnO and 35.2 ml of Hhfa are added to a flask equipped with a condenser, magnetic stirrer, and heating mantel, with stirring to disperse the ZnO. 30 ml of H$_2$O is added, causing the reflux of Hhfa due to the evolution of heat. Stirring is continued until all evidence of reaction has ceased.

An additional 30 ml of water and 200 ml of ether are then added and the mixture is refluxed for one hour. After cooling, excess ZnO is removed by filtration, the ether layer is separated and dried by the addition of 4 Å molecular sieves, and the ether is then evaporated to give 55 g of crude Zn(hfa)$_2$.2H$_2$O product.

The THF adduct of Zn(hfa)$_2$ can be prepared from this hydrated complex in accordance with the procedure set forth in Example 2 below.

EXAMPLE 2

A ten g sample of Zn(hfa)$_2$.2H$_2$O complex produced as above described is dissolved in THF at room temperature. The THF solvent is then evaporated and the residue is sublimed at 150° C. under vacuum to a dry ice-cooled cold trap. Proton nmr spectroscopic analyses of the sublimed product established that it is a THF adduct of Zn(hfa)$_2$ having the formula Zn(hfa)$_2$.nTHF, where n is in the range of about 1–2. The melting temperature of the compound as determined by differential scanning calorimetry at atmospheric pressure is 165° C. The stability of the compound is such that very slight decomposition is observed after 60 hours at the melting temperature, as evidenced by slight gas evolution and moderate discoloration of the white complex.

Figure 5:
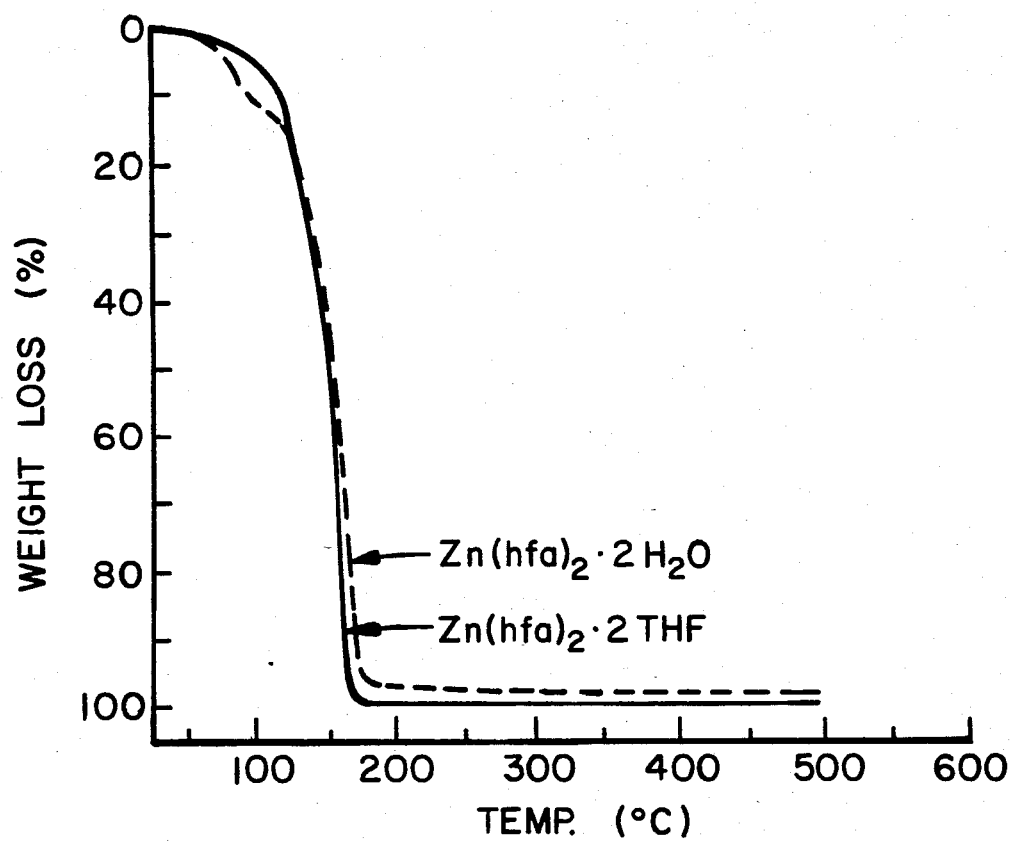
FIG. 5 contains thermogravimetric curves for selected adducted $Zn(hfa)_2$ complexes.

The superior stability and volatility of the THF adduct of Zn(hfa)$_2$ when compared with the H$_2$O adduct can be seen from FIG. 5 of the drawing. FIG. 5 sets forth thermogravimetric analysis curves for the two adducts at atmospheric pressure under argon. The data suggest that the THF adduct not only exhibits more complete vaporization than the water adduct, but also vaporizes at a lower temperature, exhibiting a T$_{178}$ temperature of 150° C. as compared with 155° C. for the water adduct.

Proton nmr spectra may be generated for the sublimed THF adduct of Zn(hfa)$_2$ as produced in accordance with Example 2 above using a TMS standard. In a case where a CDCl$_3$ solvent is used in the analysis, the data suggest the molecular formula: Zn(hfa)$_2$.1.5THF. When a d$^6$-acetone solvent is used in the analysis, the data suggest a molecular formula: Zn(hfa)$_2$.1.8THF.

Elemental chemical analyses of the sublimed THF adduct of Zn(hfa)$_2$ are conducted for F, C and Zn to confirm the number of ligands in the complex. The results of these analyses are reported in Table III below. Included in Table III are calculated percentages of C, F and Zn, assuming a molecular formula Zn(hfa)$_2$.2THF (formula weight=634 g/mole), and observed percentages for each of these elements.

TABLE III

Chemical Analysis for Zn(hfa)$_2$.2THF

| Element | % Calculated | % Observed |
|---------|--------------|------------|
| F | 36.3 | 35.0 (34.9, 35.1) |
| C | 34.6 | 34.4 (34.3, 32.8, 36.0) |
| Zn | 10.5 | 10.4 (10.6, 10.2) |

In view of the excellent agreement between the calculated and observed values in Table III, and in view of the structural analogy with Zn(hfa)$_2$.2H$_2$O, the formula Zn(hfa)$_2$.2THF is presently considered to be the correct formulation for this adducted complex.

The superior volatility and stability of the THF adducts of Mg(hfa)$_2$ and Zn(hfa)$_2$ above described make them particularly suitable candidates for applications wherein highly volatile metal complexes of these main group metals would be desirable. Such applications include the use of the compounds as metal sources in vapor phase reactions wherein transport of the metals at relatively low temperatures would be desired.

I claim:

1. A THF adduct of a β-diketone complex of 1,1,1,5,5,5-hexafluoro-2,4-pentanedione with the metal magnesium, the adduct having the molecular formula:

Mg(hfa)$_2$.$n$THF wherein n has a value of 2 or 4.

* * * * *